| United States Patent [19] | [11] Patent Number: 4,769,358 |
|---|---|
| Kishimoto et al. | [45] Date of Patent: Sep. 6, 1988 |

[54] SILVER CATALYST FOR PRODUCTION OF ETHYLENE OXIDE AND METHOD FOR MANUFACTURE THEREOF

[75] Inventors: Nobuji Kishimoto, Kawasaki; Masaharu Kiriki, Fujisawa; Minoru Saotome, Ebina, all of Japan

[73] Assignee: Nippon Shokubai Kagaku Kogyo Co., Ltd., Koraibashi, Japan

[21] Appl. No.: 930,137

[22] Filed: Nov. 12, 1986

[30] Foreign Application Priority Data

Nov. 12, 1985 [JP] Japan .................................. 60-251957
Nov. 14, 1985 [JP] Japan .................................. 60-253718

[51] Int. Cl.$^4$ .................. B01J 21/04; B01J 23/04; B01J 23/50
[52] U.S. Cl. .................................. 502/348; 502/347; 549/534
[58] Field of Search ........................... 502/347, 348

[56] References Cited

U.S. PATENT DOCUMENTS

| 4,033,903 | 7/1977 | Maxwell | 502/347 |
|---|---|---|---|
| 4,051,068 | 9/1977 | Rebsdat et al. | 502/25 |
| 4,389,338 | 6/1983 | Mitsuhata et al. | 502/348 |
| 4,471,071 | 9/1984 | Rebsdat et al. | 502/347 |

FOREIGN PATENT DOCUMENTS

| 0085237 | 8/1983 | European Pat. Off. | 502/347 |
|---|---|---|---|
| 0099975 | 2/1984 | European Pat. Off. | |
| 13137 | 6/1968 | Japan . | |
| 11217 | 4/1970 | Japan . | |
| 21373 | 7/1970 | Japan . | |
| 22419 | 7/1970 | Japan . | |
| 145677 | 11/1980 | Japan . | |
| 105750 | 8/1981 | Japan . | |
| 107241 | 7/1982 | Japan . | |
| 2002252 | 2/1979 | United Kingdom . | |
| 2045636 | 3/1980 | United Kingdom . | |
| 2117263 | 10/1983 | United Kingdom . | |

*Primary Examiner*—W. J. Shine
*Attorney, Agent, or Firm*—Omri M. Behr

[57] ABSTRACT

A silver catalyst having fine silver particles dispersed and deposited fast on the outer surface of a porous inorganic refractory carrier and on the inner wall surface of pores in said carrier and used in the production of ethylene oxide by the catalytic gas-phase oxidation of ethylene with molecular oxygen, which silver catalyst is characterized by containing a compound of at least one metal ion selected from the group consisting of cesium, rubidium, potassium, and thallium (monovalent) as dispersed and deposited fast in an amount in the range of $1 \times 10^{-6}$ to $5 \times 10^{-6}$ gram equivalent per the unit surface area, m$^2$, of said silver on the surface of said silver.

18 Claims, No Drawings

SILVER CATALYST FOR PRODUCTION OF ETHYLENE OXIDE AND METHOD FOR MANUFACTURE THEREOF

BACKGROUND OF THE INVENTION

1. Field of the Invention:

This invention relates to a silver catalyst to be used for the production of ethylene oxide by the catalytic gas-phase oxidation of ethylene with molecular oxygen and to a method for the manufacture of the silver catalyst.

2. Description of the Prior Art:

The silver catalyst which is used in the commercial production of ethylene oxide by the catalytic gas-phase oxidation of ethylene with molecular oxygen is required, for satisfactory performance of the function thereof, to exhibit high selectivity and high activity and enjoy a long catalyst life as.

Various studies have been made to date for the purpose of improving the performance of the silver catalyst and consequently fulfilling the requirement and efforts have been made to improve carriers, reaction promoters, silver compounds and the like. Numerous reports covering carriers have been published. The specifications of U.S. Pat. Nos. 3,207,700, 4,368,144, 2,766,261, 3,172,893 and 3,664,970, and the specifications of Japanese patent publication SHO No. 43(1968)-13,137, SHO No. 45(1970)-22,419 and SHO No. 45(1970)-11,217 are their examples. Most of them, however, concern pore distributions and specific surface areas of carriers.

In the specification of U.S. Pat. No. 2,125,333, there is a description to the effect that an alkali metal salt containing sodium or potassium and a metal salt thereof is used as an additive for the silver catalyst in the manufacture of ethylene oxide.

In the specification of U.S. Pat. No. 2,238,474, there is a description to the effect that sodium hydroxide improves the activity of the silver catalyst for the production of ethylene oxide and potassium hydroxide has an adverse effect upon the activity of the silver catalyst.

In the specification of U.S. Pat. No. 2,765,283, there is a description to the effect that the silver catalyst is improved by adding 1 to 2,000 ppm by weight of an inorganic chlorinated substance such as sodium chloride to the catalyst carrier before silver is deposited on the carrier.

In the specification of U.S. Pat. No. 2,799,687, there is a description to the effect that a halide such as sodium chloride or potassium chloride, used in an amount of 20 to 16,000 ppm, functions as an inhibitor and induces degradation of the activity of the silver catalyst.

In the specification of U.S. Pat. No. 4,007,135, there is disclosed a catalyst for the production of alkylene oxide, which catalyst contains copper, gold, zinc, cadmium, mercury, niobium, tantalum, molybdenum, tungsten, vanadium, or desirably chromium, calcium, magnesium, strontium, and/or more desirably barium, and preferably further an alkali metal, in an amount preceding the amount naturally present as an impurity or cement in the carrier and sufficient to manifest the action of a promoter.

In the specification of U.S. Pat. No. 4,168,247, there is disclosed a catalyst for the production of alkylene oxide, which catalyst contains silver deposited on a porous heat-resistant carrier possessing a specific surface area in the range of 0.05 to 10 $m^2/g$ and further contains sodium and at least one other alkali metal selected from the group consisting of potassium, rubidium, and cesium in a promoting amount in excess of the amount naturally present as an impurity or a binding agent in the carrier.

In the specification of U.S. Pat. No. 4,278,562, there is disclosure to the effect that a catalyst for the production of an alkylene oxide is obtained by depositing silver and optionally sodium or lithium in the form of corresponding salts on a carrier, heating the carrier and in the subsequent treatment, depositing thereon the salts of such alkali metals as potassium, rubidium, and cesium in conjunction with an amine and/or ammonia.

In Japanese Patent Laid-Open No. SHO 55(1980)-145,677, there is disclosed a silver catalyst which, as a catalyst for the reaction of oxidation, has silver and, when necessary, further an alkali metal component or an alkaline earth metal component deposited on a non-acidic carrier containing alumina, silica, and titania in a total amount of not less than 99% by weight, containing metal of the Groups Va, VIa, VIIa, VIII, Ib, and IIb of the Periodic Table of Elements in a total amount of less than 0.1% by weight, and assuming no acid color on exposure to methyl red having a pKa value of +4.8.

In Japanese Patent Laid-Open No. SHO 56(1981)-105,750, there is disclosed a silver catalyst for the production of ethylene oxide, which silver catalyst is prepared by impregnating a carrier using α-alumina as a principal component thereof and having a sodium content of not more than 0.07% by weight and a specific surface area in the range of 1 to 5 $m^2/g$ with an impregnation having 0.001 to 0.05 gram equivalent, per kg of complete catalyst, of a complex of an alkali metal with boron, a complex of an alkali metal with molybdenum, and/or a complex of an alkali metal with tungsten contained in a decomposable silver solution formulated to give a deposition ratio of 5 to 25% by weight based on the complete catalyst, and then heating and reducing or thermally decomposing the product of impregnation.

In Japanese Patent Laid-Open No. SHO 57(1982)-107,241, there is disclosed a silver catalyst for the production of ethylene oxide, which catalyst incorporates therein, besides silver, sodium (Na) as a cationic component and chlorine (Cl) as an anionic component in amounts such that the atomic ratio of Cl/Na will be less than 1.

In the specification of U.S. Pat. No. 4,415,476, there is disclosed a silver catalyst for the production of ethylene oxide, which silver catalyst contains, besides silver, at least sodium and cesium as cationic components and chlorine as an anionic component.

In Japanese Patent Laid-Open No. SHO 57(1982)-171,435, there is disclosed a silver catalyst for the production of ethylene oxide, which silver catalyst contains metallic silver particles deposited in a ratio of 5 to 25% by weight based on complete catalyst on an α-alumina carrier having a sodium content of not more than 0.07% by weight and a specific surface area in the range of 0.5 to 5 $m^2/g$ and 0.001 to 0.05 gram equivalent of at least one alkali metal or alkali metal compound per kg of the complete catalyst and in excess of the amount naturally present in the carrier.

In the specification of U.S. Pat. No. 4,248,740, there is disclosed a method for the manufacture of a silver catalyst for the production of ethylene oxide, which method is characterized by impregnating a porous inorganic refractory carrier with a silver compound containing a reducing substance, thermally reducing the resulting product of impregnation thereby causing fine silver particles to be dispersed and deposited on the outer surface of the carrier and on the inner walls of the pores in the carrier, subsequently washing the composite with water and/or a lower alcohol, drying the wet composite, further impregnating the composite with a solution of a reaction promoting substance, and evaporation the impregnated composite to dryness.

In the specification of EP No. EP-85237, there is disclosed a catalyst for the production of an alkylene oxide, which catalyst comprises silver on a porous inorganic refractory carrier containing at least 0.003 gram equivalent, per kg of complete catalyst, of cesium and/or rubidium chemically absorbed on the surface of the carrier and a catalyst wherein the amount of the chemically absorbed cesium and/or rubidium falls in the range of 400 to 3,000 ppm based on the complete catalyst per unit surface area, $m^2/g$, of the carrier.

In the specification of No. GB-2117263, there is disclosed a catalyst which comprises a granular carrier made of alumina, silica, silica-alumina, or a combination thereof, possessing a surface area approximately in the range of 0.05 to 1.5 $m^2/g$, and having a characteristic ability to absorb selectively an alkali metal from a solution of the alkali metal, 5 to 20% by weight, based on complete catalyst, of a silver dispersion deposited on the granular carrier from a solution of an organic silver salt and activated in the presence of molecular oxygen at a maximum temperature not exceeding 500° C. for a time long enough to produce an active fresh catalyst and consequently allowed to exist in the form of particles of an average particle diameter approximately in the range of 0.2 to 1.0 micron, and at least one alkali metal selected from among cesium, potassium, and rubidium deposited in an amount approximately in the range of 10 to 1,000 ppm by weight based on the complete catalyst on the dispersed active silver particles from a solution composed of water and an alkanol of 1 to 3 carbon atoms.

Numerous reports on silver catalysts have been published as described above. Most of them, however, are directed to improving the performance of silver catalyst by addition to the catalyst of an alkali metal from a specific range. All these catalysts, however, have still many problems in terms of performance and service life as a catalyst.

The effects manifested upon silver catalysts for the production of ethylene oxide by the addition thereto of reaction promoters represented by alkali metals have found recognition widely. They have been disclosed in numerous patented inventions. Most of these inventions, however, are nothing more than empirically unveiled effects. Virtually none of them has gone the length of elucidating an actual chemical action which is responsible for the effect involved. It is well known by persons skilled in the art that, owing to such true state of affairs as described above, in no few patented inventions, the inventors have disclosed contradicting technical concepts. Even in general technical literature, there are found reports such as the report written by Margolis and titled "Catalytic Oxidation of Hydrocarbons" which purport in effect that the addition of alkali metals results in degradation of the selectivity for ethylene oxide, suggesting that test results heavily hinge on methods of test adopted by individual researchers. This situation may well be regarded as a confusion arising solely from incomprehension of the true nature of chemical actions of reaction promoters. We, as the result of a diligent study, have succeeded in elucidating the chemical actions of reaction promoters and, based on the knowledge consequently acquired, perfected a literally ideal catalyst.

Various inventions have been proposed concerning kinds of reaction promoters to be used, amounts of such reaction promoters to be added for effective use, and methods of addition of such reaction promoters. The conditions in which such reaction promoters are distributed in catalysts and the actions of the reaction promoters manifested in the catalysts, however, have not been elucidated. Exceptionally, in the specifications of No. EP-85237 and No. GB-2117263, there are found statements to the effect that chemical absorption or adsorption of alkali metals on carriers is effective. These statements are interpreted as implying that the adsorption poisoning of an alkali metal done to acid sites on a carrier brings about an effect of suppressing the reaction of isomerization of ethylene oxide into acetaldehyde which is a secondary reaction in the reaction for the formation of ethylene oxide. The inventors' study has also yielded results which support these statements. It should be especially noted here, however, that in the conclusion drawn from the inventors' study, the effect of the addition of an alkali metal to the silver catalyst is manifested predominantly on the performance of silver and only secondarily on the adsorption poisoning done to the acid sites on the surface of the carrier. If the adsorption poisoning to the acid sites on the surface of the carrier is ideally realized, it does not necessarily follow that this achievement will consequently bring about a marked improvement of the performance of the catalyst (selectivity for ethylene oxide). We have confirmed that the catalyst's acquisition of an ideal performance is not realized unless the compound such as an alkali metal is deposited in an optimum amount as dispersed on the monomolecular level (with the ions of alkali metal distributed one by one independently) on the surface of silver.

In the specification of No. GB-2117263, there is found statement purporting in effect that the act of intentionally using a carrier possessing numerous acid sites for the purpose of increasing the amount of a metal to be chemically adsorbed on the carrier is effective. We are of an opinion that use of a carrier having numerous acid sites is not beneficial.

Our conclusion has drawn regarding the chemical action of a metal additive manifested on the surface of silver is that the steric hindrance effect on the surface of silver is greater than the electronic effect advocated by Margolis et al.. Margolis et al. predict that the addition of an electron donating alkali metal tends to lower the selectivity for ethylene oxide. This theory evidently contradicts the effectiveness of an alkali metal which has found recognition widely. The primary ground on which the inventors adhere to the steric hindrance effect is the fact that the adsorption such as of an alkali metal on the monomolecular level on silver contributes greatly to the improvement of selectivity. The second ground which supports their conclusion is the fact that, in addition to such heavy alkali metals as cesium, rubidium, and potassium which have already been generally accepted as effective promoters, thallium has been demonstrated by a research group including the inventors to be an equally effective promoter and all these metals possess the large cation radii in common. The four metal ions of cesium, rubidium, potassium, and thallium (monovalent) possess the four largest cation radii in all the elements excepting instable radioactive elements. In such factors as electronegativity, ionization potential, and work function which have bearing on the electron effect, these metal ions having nothing to share in common. The steric hindrance effect on the surface of silver is considered to be manifested conspicuously in the suppression of dissociative adsorption of molecular oxygen and in the suppression of readsorption of produced ethylene oxide and both the forms of suppression are believed to contribute directly to the enhancement of selectivity. Methods which define ranges of amounts of metals to be added per kg of a catalyst and ranges of amounts of metals to be added per unit surface area, m$^2$, of a carrier which are frequently found in the patented inventions published to date are extremely superficial and far from essential truths. The truth is that the performance of a catalyst is largely swayed by the condition in which a given metal additive is present in the catalyst. This is the very cause for the confusion which has brought about a wide variance among the test results obtained by different researchers. The catalysts prepared in accordance with such conventional techniques as described above are not perfectly satisfactory in performance, particularly in terms of selectivity.

An object of this invention, therefore, is to provide a novel silver catalyst for the production of ethylene oxide and a method for the manufacture of the silver catalyst.

Another object of this invention is to provide a catalyst which is enabled to acquire heretofore unattainable high selectivity and retain this quality for a long time by causing a reaction promoter of a fixed amount relative to the surface area of the silver in the catalyst to be dispersed and deposited fast on the monomolecular level on the surface of the silver and a method for the manufacture of the catalyst.

SUMMARY OF THE INVENTION

The objects described above are accomplished by a silver catalyst having fine silver particles dispersed and deposited fast on the outer surface of a porous inorganic refractory carrier and on the inner wall surfaces of pores in the carrier and used in the production of ethylene oxide by the catalytic gas-phase oxidation of ethylene with molecular oxygen, which silver catalyst is characterized by containing a compound of at least one metal ion selected from the group consisting of cesium, rubidium, potassium, and thallium (monovalent) as dispersed and deposited fast in an amount in the range of $1 \times 10^{-6}$ to $5 \times 10^{-6}$ gram equivalent per unit surface area, m$^2$, of silver on the surface of the silver.

These objects are accomplished by a method for the manufacture of a silver catalyst having fine silver particles dispersed and deposited fast on the outer surface of a porous inorganic refractory carrier and on the inner wall surfaces of pores in the carrier and used in the production of ethylene oxide by the catalytic gas-phase oxidation of ethylene with molecular oxygen, which method comprises impregnating the porous inorganic refractory carrier with a solution of a silver compound containing a reducing compound, thermally reducing the product of impregnation thereby enabling fine silver particles to be dispersed and deposited fast on the outer surface of the porous inorganic refractory carrier and on the inner wall surface of pores in the carrier, subsequently washing the resulting composite with at least one member selected from the group consisting of water and a lower alcohol, drying the wet composite, and subsequently causing a compound of at least one metal ion selected from the group consisting of cesium, rubidium, potassium, and thallium (monovalent) to be dispersed and deposited fast in an amount in the range of $1 \times 10^{-6}$ to $5 \times 10^{-6}$ gram equivalent per the unit area, m$^2$, of the silver on the surface of the silver, wherein said dispersion and deposition are effected by adsorption from an impregnant containing the compound of at least one metal selected from the group consisting of cesium, rubidium, potassium, and thallium (monovalent) and the impregnation and the expulsion of the solvent by drying subsequent to the step of adsorption and deposition are carried out at temperatures not exceeding 50° C.

The aforementioned objects are also accomplished by a method for the manufacture of a silver catalyst having fine silver particles dispersed and deposited fast on the outer surface of a porous inorganic refractory carrier and on the inner wall surface of pores in the carrier and used in the production of ethylene oxide by the catalytic gas-phase oxidation of ethylene with molecular oxygen, which method comprises impregnating the porous inorganic refractory carrier with a solution of a silver compound containing a reducing compound, thermally reducing the product of impregnation thereby enabling fine silver particles to be dispersed and deposited fast on the outer surface of the porous inorganic refractory carrier and on the inner wall surface of pores in the carrier, then heating the resulting composite in a current of gas at a temperature exceeding 200° C. thereby decomposing and expelling the residual organic substance, and subsequently causing at least one metal ion selected from the group consisting of cesium, rubidium, potassium, and thallium (monovalent) to be dispersed and deposited fast in an amount in the range of $1 \times 10^{-6}$ to $5 \times 10^{-6}$ gram equivalent per the unit area, m$^2$, of the silver on the surface of the silver, wherein said dispersion and deposition are effected by adsorption from an impregnant containing the compound of at least one metal selected from the group consisting of cesium, rubidium, potassium, and thallium (monovalent) and the impregnation and the expulsion of the solvent by drying subsequent to the step of adsorption and deposition are carried out at temperatures not exceeding 50° C.

DESCRIPTION OF PREFERRED EMBODIMENT

We have found that for notably improvment of the selectivity of a silver catalyst, the cesium compound, for example, must be dispersed and deposited in an optimum amount on the monomolecular level on the surface of silver. With the conventional technique, however, it is extremely difficult to realize the deposition of the cesium compound in the particular manner just mentioned. Any catalyst answering this description has never existed in fact. To effect the dispersion and deposition of the cesium compound in the manner described above, use of the action of adsorption is advantageous. Unlike the conventional technique which effects adsorption by making use of acid sites on a carrier, fast retention of the cesium compound, for example, in a dispersed and deposited state on a completed catalyst requires fixation of special conditions because strong adsorption sites necessary for chemical adsorption do not exist on silver.

When a silver catalyst, no matter whether it may be used as deposited on a carrier or not, is kept immersed for a long time in a solution containing a cesium compound, for example, the solution is observed to vary its concentration and reach an equilibrium concentration in a fixed length of time (mostly in 3 to 4 hours) and, as the result, a solute exceeding the concentration of the solution is seen to be deposited on silver. It may be safely concluded that this phenomenon constitutes one form of adsorption. This adsorption, however, is very weak so that the deposited solute will readily separate from the silver when it is treated with a solvent of a high dissolving power. Further, the amount of the solute adsorbed on the silver is notably decreased when the temperature of the impregnant is elevated.

We have experimentally confirmed that the relation between the amount of the monovalent ion such as $Cs^+$ ion adsorbed and the equilibrium concentration of the solution can be regulated by Langmuir Formula of Adsorption, indicating that the adsorption is a monomolecular layer adsorption and possesses the nature of chemical adsorption. On the other hand, the amount of saturated adsorption found by the test equals the amount required for covering the surface of silver substantially completely. This fact indicates that the adsorption sites involved in this case are not limited to any special cites on the surface of silver. From these test results, we have concluded the phenomenon of adsorption under discussion to be an action of electrostatic adsorption occurring between the adsorbed oxygen $O^-$ normally present on the surface of silver and the monovalent metal ion such as $Cs^+$ ion. When this weak adsorption is utilized for the dispersion and deposition of the monovalent metal ion, the process for the preparation of a silver catalyst necessitates fixation of special conditions.

The conditions to be observed for the process are as follows.

(1) While the impregnate containing a monovalent metal ion such as cesium ion requires to contain the solute in a prescribed amount, it should be prepared using a solvent in which the solute has as low solubility as possible. In water, for example, cesium and other similar monovalent compounds have excessively high degrees of solubility. It is, therefore, not desirable to use water along as the solvent. Cesium and other similar monovalent compounds can be used in the form of oxalates, carbonates, acetates, and other salts, oxides, and hydroxides. Desirably as the solvent, a lower alcohol of not more than 3 carbon atoms or a mixed solvent thereof is used.

(2) The immersion in the solution of the monovalent metal ion such as cesium ion or other similar monovalent metal ion should be carried out at a low temperature of less than 50° C. This temperature is desired to fall in the range of 0° to 40° C., preferably 0° to 25° C. When the immersion is made at higher temperatures, the amount of adsorption is notably decreased and the performance of the produced catalyst is degraded.

(3) The expulsion of the solvent by drying should be carried out at a low temperature of less than 50° C. It is desired to be made in a current of gas at a temperature not higher than the immersion temperature. When the immersion is made at a low temperature as described above but, in the subsequent step, the drying treatment is carried out at a high temperature, the adsorbed ions are separated from the silver during the course of the drying treatment, with the result that the amount of adsorption will be notably decreased and the performance of the produced catalyst will be degraded.

When these conditions are selected, there is obtained a silver catalyst containing a cesium compound, for example, dispersed and deposited fast on the monomolecular level on the surface of silver. For the produced silver catalyst to acquire the optimum performance, the amount of cesium ion or other similar monovalent ion to be dispersed and deposited on the silver should be limited to a level falling in the range of $1 \times 10^{-6}$ to $5 \times 10^{-6}$ gram equivalent, preferably $1.5 \times 10^{-6}$ to $4 \times 10^{-6}$ gram equivalent, per the unit area, $m^2$, of the surface of silver. The concentration of the impregnant which is required in fixing the amount of deposition of the cesium compound, for example, within the range can be easily found from the linear formula derivable from the Langmuir's adsorption isotherm to be obtained with respect to the adsorption on the surface of silver. If the cesium compound is dispersed and deposited in any amount exceeding the aforementioned range on the surface of silver, the produced catalyst possesses notably low activity. If this amount falls short of the lower limit of the range, then the produced catalyst possesses notably inferior selectivity.

When the method of this invention is followed, the monovalent metal compound such as cesium compound, for example, is deposited also on the exposed surface of the carrier. The aforementioned range, however, has absolutely nothing to do with the amount of the cesium compound to be deposited on the exposed surface of the carrier. This range is applied exclusively to the amount of the monovalent metal compound such as cesium compound, for example, which is deposited on the surface of silver. The amount of the monovalent metal compound which has been dispersed and deposited on the monomolecular level on the surface of silver by virtue of adsorption is determined as follows.

First, the amount, A (gram equivalent), of the monovalent metal compound such as the cesium compound adsorbed on the entire surface of silver is calculated as follows.

$$A = \{(\text{Concentration of prepared impregnant}) - (\text{Equilibrium concentration of impregnant for adsorption})\} \times (\text{Amount of impregnant}) \quad (1)$$

The amount, A includes the amount of the impregnant adsorbed on the exposed surface of the carrier besides the amount of the impregnant adsorbed on the surface of silver. Then, the carrier from the same lot in the same amount as used in the preparation of the catalyst is subjected to the same procedure as used in the preparation of the catalyst, excepting the deposition of silver is omitted. The carrier is then immersed in a solution containing the cesium ion, for example, in a varying concentration, to obtain data on the relation between the equilibrium concentration for adsorption and the amount of adsorption. The data so obtained can be regulated by Langmuir's adsorption formula. The amount of adsorption on the surface of the carrier obtained in the same equilibrium concentration for adsorption as the equilibrium concentration for adsorption with the catalyst is calculated similarly to the formula (1). The amount thus calculated is reported as B (gram equivalent).

Let $S_A$ ($m^2$/g of catalyst) stand for the specific surface area of the catalyst found by the BET (Brunauer-Emmett-Teller) method, $S_B$ ($m^2$/g of carrier) for the specific surface area of the carrier to be used, and a (wt%) [=(weight of catalyst−weight of carrier)/ weight of catalyst×100] for the silver content of the catalyst, then the surface area, $S_A'$ ($m^2/g$ of catalyst), or silver in the catalyst on the assumption that silver particles have a hemispheric shape will be found as follows:

$$S_A' = 2\{S_A - S_B \times (100-a)/100\}$$

The surface area of the exposed carrier, $S_B'$ ($m^2/g$ of catalyst), in the catalyst is found as follows:

$$S_B' = S_A - S_A'$$

Consequently, the amount of the cesium compound, $A'$ (gram equivalent), adsorbed on the surface of silver is found as follows:

$$A' = A - B \times (S_B' \times \text{weight of catalyst}) (S_B \times \text{weight of carrier})$$

Then, the amount of the cesium compound adsorbed per unit area, $m^2$, of the surface of silver, C (gram equivalent/$m^2$ of Ag), is found as follows:

$$C = A'(S_A' \times \text{weight of catalyst})$$

Since the relation between the amount of adsorption, $A'$, on the surface of silver and the equilibrium concentration of the impregnant for adsorption to be found by the method of calculation indicated above can also be regulated by Langmuir type adsorption formula, the adsorption on the surface of silver is a monomolecular layer adsorption. The amount of saturated adsorption to be found from Langmuir type formula substantially agrees with the amount to be found geometrically from the ion radius of cesium or other similar monovalent metal. This fact proves that the adsorption under discussion is an adsorption on the molecular level.

The effect of the addition of cesium or other similar monovalent metal on the carrier is considered to reside in poisoning the acid sites on the surface of the carrier thereby suppressing the activity of isomerization of ethylene oxide. This conclusion can be proved by the following experiment, for example. When ethylene is oxidized in a reaction tube packed with the catalyst of this invention and the outlet gas containing the produced ethylene oxide is passed through another reaction tube packed solely with a carrier of the same amount as the catalyst in the first reaction tube and held at the same temperature as the first reaction tube, the ratio of isomerization of ethylene oxide calculated from the change of gas composition at the inlet and the outlet of the second reaction tube shows loss of 1 to 4% of inlet ethylene oxide, depending on the kind of the carrier used. When the same test is performed using a carrier having a proper amount of cesium compound, for example, dispersed and deposited therein, the loss of inlet ethylene oxide is only less than 1%. The results clearly show the effect of the addition of the cesium compound, for example, to the carrier. In due consideration of the fact that the exposed surface of the carrier relative to the surface of the catalyst is considerably smaller than the surface of the carrier used alone, the effect of the addition to the carrier is believed to be not more than about 2% in terms of the selectivity for ethylene oxide. The inventors, in this respect, wish to emphasize strongly the fact that then the cesium compound is dispersed and deposited in a suitable amount on the surface of silver in accordance with the present invention, there can be realized a plus effect of more than 10% in terms of selectivity for ethylene oxide.

When the adsorption of the cesium compound is carried out from a solution, the solute in the solution remaining within the pores adheres to the inner wall of the pores. The portion of the monovalent metal compound such as cesium compound thus deposited inside the pores is not included in the monovalent metal compound dispersed and deposited as defined herein. The expression "cesium compound, for example, dispersed and deposited" as used herein refers to the cesium compound deposited on the monomolecular level (with the cesium ions distributed independently one by one). The solute which has settled inside the pores are not dispersed or deposited but allowed to remain in the form of clusters of certain size. Since these clusters bring about no beneficial effect and, when occurring excessively, go to impairing the performance of the catalyst, it is desirable to reduce the amount of clusters to the fullest possible extent. For successful control of the clusters, it is necessary to observe faithfully the three conditions mentioned above, lower the concentration of the solution to the irreducible minimum, and keep down the equilibrium concentration for adsorption as much as possible. When these conditions are fulfilled, the amount of the monovalent metal compound entrapped inside the pores can be suppressed to the order of about 20% of the amount deposited by adsorption, so that the clusters of monovalent metal compound cannot have any noticeable adverse effect upon the performance of the catalyst. If these conditions are not fulfilled, the proportion accounted for by the amount of the monovalent metal compound entrapped increases possibly to the extent of impairing the performance of the catalyst. Another method conceivable for lowering the effect of the monovalent metal compound clusters entrapped in the pores comprises immersing the catalyst as a finished product in a solvent thereby allowing the entrapped clusters of monovalent metal compound to be preferentially dissolved out. This method, however, cannot be called desirable because it is not easy to determine and control the adsorbed amount of monovalent metal compound.

For more effective manifestation of the effect of this invention, the silver deposited on the carrier is desired to be in a highly dispersed state. By covering the surface of the carrier with silver particles and consequently decreasing the exposed surface of the carrier, the effect of the active sites on the surface of the carrier can be decreased and the possible dilution of the effect of this invention can be avoided.

The catalyst contemplated by the present invention is prepared as follows.

As the solution of a silver compound containing a reducing compound and used for the present invention, any of all the known solutions answering the description can be adopted. Among other solutions available at all, those which permit high dispersion of silver advantageously are solutions containing alkanolamine as a reducing compound and having various silver compounds dissolved in alkanolamine or other amine, an aqueous silver nitrate solution containing formaline as a reducing component, and monoethylene glycol solutions of silver nitrate containing lower acid amides as reducing components.

As typical examples of alkanolamine or other amine to be used as the reducing compound, there can be cited mono-, di-, and triethanolamines, mono-, di-, and tri-n- propanolamines, mono-, di- and tri-isopropanolamines, n-butanolamines, and isobutanolamines. As typical examples of the lower acid amide, there can be cited foramide, acetamide, propionic acid amide, glycolic acid amide, and dimethylformamide.

As the silver salt to be used as a starting material, any of the inorganic silver salts and organic silver salts which are capable of reacting the alkanolamine and consequently forming a complex salt can be adopted. Typical examples of the silver salt include silver nitrate, silver carbonate, silver sulfate, silver acetate, silver oxalate, silver lactate, silver succinate, and silver glycolate.

As the solvent to be used in this invention, water proves desirable. A lower aliphatic compound of 2 to 6 carbon atoms containing 1 to 3 alcoholic hydroxyl groups in the molecular unit thereof is advantageously used particularly when a lower acid amine is used as a reducing compound. Examples of the lower aliphatic compound include monoethylene glycol, diethylene glycol, triethylene glycols, trimethylene glycol, monopropylene glycol, methyl cellosolve, ethyl cellosolve, methyl carbitol, ethyl carbitol, and glycerol.

The solution of a silver compound selected from among those described above is used to impregnate a porous inorganic carrier.

As the porous inorganic carrier to be used for this invention, any of the porous inorganic carriers heretofore known to the art can be adopted. Among other carriers available at all, a carrier made of alumina and/or silica proves particularly desirable. Especially, a carrier made of α- alumina gives favorable results. This carrier is desired to have an apparent porosity in the range of 40 to 70%, preferably 50 to 65%, and a BET specific surface area in the range of 0.1 to 10 $m^2/g$, preferably 0.2 to 5 $m^2/g$.

The silver compound containing the reducing compound, at a temperature in the range of room temperature to 200° C. is reduced to metallic silver and deposited in the form of fine particles on the inner and outer surfaces of the carrier. In this case, the heating temperature is desired to be kept down to the irreducible minimum. Better results of the heating are obtained when the heating is started at a low temperature and then continued at gradually elevated temperatures.

After the active silver has been dispersed and adhered fast on the outer surface of the carrier and on the inner surface of pores in the carrier, the resulting composite is washed with water and/or a lower alcohol preferably in a boiling condition. Examples of the lower alcohol are aliphatic alcohols of 1 to 3 carbon atoms, such as methanol, ethanol, isopropanol, and n-propanol. This washing treatment is effective in removing alkanolamine and other organic substances from the catalyst and, at the same time, cleaning the surface of the produced active silver and enhancing the activity of the silver. The amount of silver to be deposited is desired to fall in the range of 2 to 25% by weight, preferably 5 to 20% by weight, based on the complete catalyst. The washed composite is then dried by being heated to a temperature in the range of 50° to 150° C. The catalyst obtained consequently has deposited on the carrier fine and uniform silver particles having an average diameter not exceeding 1,000 Angstroms.

Instead of washing and drying the composite described above after silver compound has been reduced to metallic silver, the remained organic compound may be removed by heating this composite in a current of a gas, suitably an inert gas such as nitrogen at a temperature exceeding 200° C., desirably falling in the range of 200° to 300° C. to activate the catalyst. The heating effected in an atmosphere containing oxygen at a high temperature exceeding 300° C. is undesirable because it entails heavy sintering of silver particles. It is desirable to adopt conditions such that the average diameter of the silver particles will fall not more than 2,000 Angstroms, preferably 1,000 Angstroms. Again in this case, the amount of silver to be deposited is desired to fall in the range of 2 to 25% by weight, preferably 5 to 20% by weight, based on the complete catalyst.

Further, the catalyst consequently produced is immersed in a solution of a compound of at least one metal selected from the group consisting of cesium, rubidium, potassium, and thallium (monovalent) in a lower alcohol such as methanol or ethanol, for example, so that the compound of at least one metal selected from the group consisting of cesium, rubidium, potassium, and thallium (monovalent) will be dispersed and deposited fast in an amount in the range of $1 \times 10^{-6}$ to $5 \times 10^{-6}$ gram equivalent per the unit area, $m^2$ of the silver on the surface of silver. In this case, the immersion is made at a temperature of less than 50° C., desirably in the range of 0° to 40° C., and more desirably 0° to 25° C. The expulsion of the solvent by drying after the deposition by adsorption is carried out at a temperature of less than 50° C., desirably in the range of 0° to 40° C., and more desirably 0° to 25° C. This expulsion of the solvent is desirably carried out in a current of a gas.

The compounds of cesium, rubidium, potassium, and thallium (monovalent) are used in the form of nitrates, sulfates, carbonates oxalates, hydroxides, oxides, and acetates.

Examples of the lower alcohol to be used as a solvent include methanol, ethanol, isopropanol, n-propanol, and mixtures thereof.

As the conditions to be used in the method for manufacture of ethylene oxide by the catalytic gas-phase oxidation of ethylene with molecular oxygen in the presence of a silver catalyst obtained by the present invention, all the conditions heretofore known in the art can be adopted. The conditions generally adopted for the commercial production of ethylene oxide, i.e. the reaction temperature in the range of 150° to 300° C., preferably 180° to 280° C., the reaction pressure in the range of 2 to 40 kg/cm$^2$G, preferably 10 to 30 kg/cm$^2$G, and the space velocity in the range of 1,000 to 30,000 hr$^{-1}$ (STP), preferably 3,000 to 8,000 hr$^{-1}$ is desirably composed of 0.5 to 30% by volume of ethylene, 5 to 30% by volume of carbon dioxide gas, and the balance to make up 100% by volume of an inert gas such as nitrogen, argon, or steam, and a low hydrocarbon such as methane or ethane preferably plus 0.1 to 10 ppm (volume) of a halide such as ethylene dichloride, diphenyl chloride, vinyl chloride, monochlorobenzene or dichlorobenzene which is intended as a reaction inhibitor.

Examples of the source of molecular oxygen to be used in the present invention, there can be cited air, oxygen, and oxygen enriched air.

The chemical action of dispersion and deposition of the cesium ion on the surface of silver is believed to produce a notable steric hindrance effect upon various adsorbates on the surface of silver during the oxidation of +ethylene. One phase of this effect is manifested on adsorbates of oxygen species by effectively coating adjacent silver atoms and thereby curbing dissociative adsorption of oxygen and suppressing complete oxidation. Another phase of the effect is manifested in curbing and readsorption of the produced ethylene oxide on silver and suppressing the isomerization of ethylene oxide into acetaldehyde. In both the phases, the effect is believed to contribute directly to enhancing the selectivity for ethylene oxide.

Now, the present invention will be described more specifically below with reference to working examples and controls. It should be noted that the examples are purely illustrative of, and not limitative in any sense of, the present invention.

The numerical values of conversion and selectivity to be indicated in the working examples and the controls are the results of calculation based on the following formulas.

$$\text{Conversion (\%)} = \frac{\text{Number of mols of ethylene reacted}}{\left(\begin{array}{c}\text{Number of mols of ethylene} \\ \text{in feed gas}\end{array}\right)} \times 100$$

$$\text{Selectivity} = \frac{\left(\begin{array}{c}\text{Number of mols of ethylene} \\ \text{converted to ethylene oxide}\end{array}\right)}{\left(\begin{array}{c}\text{Number of mols of} \\ \text{ethylene reacted}\end{array}\right)} \times 100$$

EXAMPLE 1

A silver impregnant was prepared by dissolving 470 g of silver nitrate in 300 g of water, keeping the solution cooled in a water bath, adding 360 g of ethanolamine to the solution, and thoroughly stirring the resulting mixture. In this impregnant was immersed 2.2 liters of α-alumina carrier having an apparent porosity of 57% and a BET specific surface area of 0.78 m$^2$/g. The impregnation mixture was gradually heated to 90° C., stirred at this temperature for 3 hours, heated further to 120° C., and stirred for 2 hours so as to have the reduced silver dispersed and deposited on the carrier. The silver-deposited catalyst thus obtained was washed five times with 3 liters of boiling water and then dried by heating in a current of nitrogen at 110° to 120° C. for 4 hours.

Then, the dried catalyst was kept immersed in a solution of 1.60 g of cesium carbonate in 1,615 ml of reagent grade ethanol at 20° C. for 3 hours. Subsequently, the catalyst was deprived of excess impregnant and further swept with dry nitrogen flowing at a rate of 50 liters/minute for 5 hours for thorough evaporation and expulsion of the solvent remaining in the pores of the carrier. In this while, the temperature of the catalyst was prevented from exceeding 20° C.

The catalyst obtained at this point was found to have 13.5% by weight of silver deposited thereon. The surface area of this silver was 1.03 m$^2$/g of catalyst, the exposed surface area of the carrier was 0.14 m$^2$/g of catalyst, and the amount of cesium ion deposited by adsorption on the surface of silver was $2.3 \times 10^{-6}$ gram equivalent per the unit area, m$^2$, of the surface of the silver.

An externally heating type double-pipe stainless steel reactor 25 mm in inside diameter and 6,000 mm in length was packed with the catalyst. A mixed feed gas consisting of 20% by volume of ethylene, 8% by volume of oxygen, 7% by volume of carbon dioxide gas, and the balance to make up 100% by volume of methane, nitrogen, argon, and ethane and further containing 2 ppm of ethylene dichloride was introduced into the catalyst bed and left reacting under a reaction pressure of 15 kg/cm$^2$G at a space velocity of 6,500 hr$^{-1}$. The results obtained after 30 days reaction are shown in Table 1. Even after 6 months' continued reaction, this catalyst retained the performance intact.

EXAMPLE 2

A catalyst was prepared following the procedure of Example 1, except that a solution of 1.25 g of rubidium carbonate in 1,615 ml of reagent grade methanol was used in place of the solution of 1.60 g of cesium carbonate in 1,615 ml of reagent grade ethanol. The catalyst thus obtained was found to have 13.5% by weight of silver deposited thereon. The surface area of the silver was 1.03 m$^2$/g of catalyst, the exposed surface area of the carrier was 0.14 m$^2$/g of catalyst, and the amount of rubidium ion deposited by adsorption on the silver was $2.6 \times 10^{-6}$ gram equivalent per the unit area, m$^2$, of the surface of the silver.

When oxidation of ethylene was carried out by using this catalyst following the procedure of Example 1, the results after 30 days of reaction were as shown in Table 1. Even after 6 months' continued reaction, this catalyst retained the performance thereof intact.

EXAMPLE 3

A catalyst was prepared following the procedure of Example 1, except that a solution of 1.30 g of potassium nitrate in 1,615 ml of reagent grade methanol was used in the place of the solution of 1.60 g of cesium carbonate in 1,615 ml of reagent grade ethanol. The catalyst thus obtained was found to have 13.5% by weight of silver deposited thereon. The surface area of the silver was 1.03 m$^2$/g, the exposed surface area of the carrier was 0.14 m$^2$/g, and the amount of potassium ion deposited by adsorption on the silver was $2.8 \times 10^{-6}$ gram equivalent per the unit area, m$^2$, of the surface of the silver.

When oxidation of ethylene was carried out by using this catalyst following the procedure of Example 1, the results of 30 days' reaction were as shown in Table 1. Even after 6 months' continued reaction, this catalyst retained the performance thereof intact.

EXAMPLE 4

A catalyst prepared following the procedure of Example 1, except that 2.45 g of thallium acetate was used in place of 1.60 g of cesium carbonate. The catalyst thus obtained was found to have 13.5% by weight of silver deposited thereon. The surface area of the silver was 1.03 m$^2$/g of catalyst, the exposed surface area of the carrier was 0.14 m$^2$/g of catalyst, and the amount of thallium (monovalent) ion deposited by adsorption on the silver was $2.7 \times 10^{-6}$ gram equivalent per the unit area, m$^2$, of the surface of the silver.

When oxidation of ethylene was carried out by using this catalyst following the procedure of Example 1, the results of 30 days' reaction were as shown in Table 1. Even after 6 months' continued reaction, this catalyst retained the performance thereof intact.

EXAMPLE 5

A catalyst was prepared following the procedure of Example 1, except that an α-alumina carrier having an apparent porosity of 54% and a BET specific surface area of 1.12 m$^2$/g was used instead and a solution of 2.40 g of cesium carbonate in 1,600 ml of reagent grade ethanol was used in place of the solution of 1.60 g of cesium carbonate in 1,615 ml of reagent grade thanol. The catalyst thus obtained was found to have 13.5% by weight of silver deposited thereon. The surface area of the silver was 1.25 m²/g of catalyst, the exposed surface area of the carrier was 0.36 m²/g of catalyst, and the amount of cesium ion deposited by adsorption on the silver was $2.9 \times 10^{-6}$ gram equivalent per the unit area, m², of the surface of the silver.

When oxidation of ethylene was carried out by using this catalyst following the procedure of Example 1, the results of 30 days' reaction were as shown in Table 1. Even after 6 months' continued reaction retained the performance thereof intact.

EXAMPLE 6

A silver-containing impregnant was prepared by dissolving 520 g of silver nitrate in 300 g of water, keeping this solution cooled in a water bath, adding 400 g of ethanolamine to the cooled solution, and thoroughly stirring the resulting mixture. In this impregnant was immersed 2.2 liters of α-alumina carrier having an apparent porosity of 60% and a BET specific surface area of 2.80 m²/g. The impregnation mixture was gradually heated to 90° C., stirred at this temperature for 3 hours, further heated to 120° C., and stirred for 2 hours to have the reduced silver dispersed and deposited on the carrier. The silver-deposited catalyst consequently obtained was washed five times with 3 liters of boiling water and was then dried by heating in a current of nitrogen at 110° to 120° C. for 4 hours.

Then, the dried catalyst was kept immersed in a solution of 4.65 g of cesium carbonate in 1,650 ml of reagent grade ethanol at 20° C. for 3 hours. Subsequently, the catalyst was deprived of excess impregnant and further swept with dry nitrogen flowing at a flow rate of 50 liters/minute for 5 hours thorough evaporation and expulsion of the solvent remaining within the pores of the carrier. In this while, the temperature of the catalyst was prevented from exceeding 20° C.

The catalyst thus obtained was found to have 14.7% by weight of silver deposited thereon. The surface area of the silver was 2.42 m²/g of catalyst, the exposed surface area of the carrier was 1.18 m²/g of catalyst, and the amount of cesium ion deposited by adsorption on the silver was $2.1 \times 10^{-6}$ gram equivalent per the unit area, m², of the surface of the silver.

When oxidation of ethylene was carried out by using this catalyst following the procedure of Example 1, the results of 30 days' reaction were as shown in Table 1. Even after 6 months' continued reaction, the catalyst retained the performance thereof intact.

EXAMPLE 7

A catalyst was prepared following the procedure of Example 6, excepting 320 g of water was used in place of 300 g of water, an α-alumina carrier having an apparent porosity of 62% and a BET specific surface area of 3.53 m²/g was used instead, and a solution of 5.10 g of cesium carbonate in 1,680 ml of reagent grade ethanol was used in place of the solution of 4.65 g of cesium carbonate in 1,650 ml of reagent grade ethanol. The catalyst thus obtained was found to have 14.8% by weight of silver deposited thereon. The surface area of the silver was 2.86 m²/g of catalyst, the exposed surface area of the carrier was 1.58 m²/g of catalyst, and the amount of cesium ion deposited by adsorption on the silver was $2.0 \times 10^{-6}$ gram equivalent per the unit area, m², of the surface of the silver.

When oxidation of ethylene was carried out by using this catalyst following the procedure of Example 1, the results of 30 days' reaction were as shown in Table 1. Even after 6 months' continued reaction, this catalyst retained the performance thereof intact.

EXAMPLE 8

A silver impregnant was prepared by dissolving 470 g of silver nitrate in 300 g of water, keeping the solution cooled in a water bath, adding 360 g of ethanolamine to the cooled solution, and thoroughly stirring the resulting mixture. In the impregnant was immersed 2.2 liters of α-alumina carrier having an apparent porosity of 57% and a BET specific surface area of 0.78 m²/g. This impregnation mixture was gradually heated to 90° C., stirred at this temperature for 3 hours, then heated further to 120° C., and stirred for 2 hours so as to have the reduced silver dispersed and deposited on the carrier. The silver-deposited catalyst consequently obtained was washed 5 times with 3 liters of boiling water and then heated in a current of nitrogen at 110° to 120° C. for 4 hours.

Subsequently, the dried catalyst was kept immersed in a solution of 1.60 g of cesium carbonate in 1,615 ml of reagent grade ethanol of 0° C. for 3 hours. Then, the catalyst was deprived of excess impregnant and swept with dry nitrogen flowing at a rate of 50 liters/minute for 8 hours thorough evaporation and expulsion of the solvent remaining in the pores of the carrier. In this while, the temperature of the catalyst was prevented from exceeding 0° C.

The catalyst consequently obtained was found to have 13.5% by weight of silver deposited thereon. The surface area of this silver was 1.03 m²/g of catalyst, the exposed surface area of the carrier was 0.14 m²/g of catalyst, and the amount of cesium ion deposited by adsorption on the silver was $2.4 \times 10^{-6}$ gram equivalent per the unit area, m², of the surface of the silver.

When oxidation of ethylene was carried out by using this catalyst following the procedure of Example 1, the results of 30 days' reaction were as shown in Table 1. Even after 6 months' continued reaction, this catalyst retained the performance thereof intact.

EXAMPLE 9

A silver impregnant was prepared by dissolving 470 g of silver nitrate in 700 g of monoethylene glycol, adding 190 g of formaldehyde to the solution, and thoroughly stirring the resulting mixture. In the impregnant was immersed 2.2 liters of α-alumina carrier having an apparent porosity of 57% and a BET specific surface area of 0.78 m²/g. This impregnation mixture was stirred and, at the same time, heated to 130° C., stirred at this temperature for 2 hours, further heated to 160° C., and stirred for 2 hours so as to have the reduced silver dispersed and deposited on the carrier. The silver-deposited catalyst consequently obtained was washed 8 times with boiling water and then dried by heating in a current of nitrogen at 110° to 120° C. for 4 hours.

The dried catalyst was kept immersed in a solution of 1.45 g of cesium carbonate in 1,615 ml of reagent grade ethanol at 20° C. for 3 hours. Then, the catalyst was deprived of excess impregnant and swept with dry nitrogen flowing at a rate of 50 liters/minute for 5 hours for thorough evaporation and expulsion of the solvent remaining inside the pores of the carrier. In this while, the temperature of the catalyst was prevented from exceeding 20° C.

The catalyst consequently obtained was found to have 13.5% by weight of silver deposited thereon. The surface area of this silver was 0.91 $m^2/g$ of catalyst, the exposed surface area of the carrier was 0.22 $m^2$ catalyst, and the amount of cesium ion deposited by adsorption on the silver was $2.3 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 1. Even after 6 months' continued reaction, this catalyst retained the performance thereof intact.

CONTROL 1

A silver impregnant was prepared by dissolving 470 g of silver nitrate in 300 g of water, keeping the solution cooled in a water bath, adding 360 g of ethanolamine to the cooled water, and thoroughly stirring the resulting mixture. In the impregnant was immersed 2.2 liters of α-alumina carrier having an apparent porosity of 57% and a BET specific surface area of 0.78 $m^2/g$. This impregnation mixture was gradually heated to 90° C., stirred at this temperature for 3 hours, then heated further to 120° C., and stirred for 2 hours so as to have the reduced silver dispersed and deposited on the carrier. The silver-deposited catalyst consequently obtained was washed 5 times with 3 liters of boiling water and then dried by heating in a current of nitrogen at 110° to 120° C. for 4 hours.

Then, the dried catalyst was kept immersed in a solution of 5.05 of cesium carbonate in 1615 ml of reagent grade ethanol at 20° for 3 hours. Subsequently, the catalyst was deprived of excess impregnant and further swept with dry nitrogen flowing at a flow rate of 50 liters/minute for 5 hours for thorough evaporation and expulsion of the solvent remaining within the pores of the carrier. In this while, the temperature of the catalyst was prevented from exceeding 20° C.

The catalyst thus obtained was found to have 13.5% by weight of silver deposited thereon. The surface area of the silver was 1.03 $m^2/g$ of catalyst, the exposed surface area of the carrier was 0.14 $m^2/g$ of catalyst, and the amount of cesium ion deposited by adsorption on the silver was $5.5 \times 10^{-6}$ gram equivalent per the unit area, $m^2$, of the surface of the silver.

When oxidation of ethylene was carried out by using this catalyst following the procedure of Example 1, the result of 30 days' reaction were as shown in Table 1.

CONTROL 2

A catalyst was prepared following the procedure of Control 1, except that 0.24 g of cesium carbonate was used in place of 5.05 g of cesium carbonate.

The catalyst thus obtained was found to have 13.5% by weight of silver deposited thereon. The surface area of this silver was 1.03 $m^2/g$ of catalyst, the exposed surface area of the carrier was 0.14 $m^2/g$ of catalyst, and the amount of cesium ion deposited by adsorption on the silver was $0.4 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 1.

CONTROL 3

A catalyst was obtained by following the procedure of Control 1, except that 1.45 g of cesium carbonate was used in place of 5.05 g of cesium carbonate, the carrier was kept immersed in the ethanol solution of cesium carbonate at 70° C. for 3 hours, and the outer wall temperature of the catalyst bed during the evaporation and expulsion of the solvent retained in the pores of the carrier was kept at 70° C.

The catalyst thus obtained was found to have 13.5% by weight of silver deposited thereon. The surface area of the silver was 1.03 $m^2/g$ of catalyst, the exposed surface area of the carrier was 0.14 $m^2/g$ of catalyst, and the amount of cesium ion deposited by adsorption on the silver was $0.8 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 1. After six months' continued reaction using this catalyst, the reaction temperature increased 2° C. and the selectivity decreased to 73.2%.

TABLE 1

| | Example | | | | | |
|---|---|---|---|---|---|---|
| | 1 | 2 | 3 | 4 | 5 | 6 |
| Specific surface area of carrier ($m^2/g$) | 0.78 | 0.78 | 0.78 | 0.78 | 1.12 | 2.80 |
| Apparent porosity of carrier (%) | 57 | 57 | 57 | 57 | 54 | 60 |
| Impregnant (Solute) containing metal compound | cesium carbonate | rubidium carbonate | potassium nitrate | thallium acetate | cesium carbonate | cesium carbonate |
| (Solvent) | ethanol | methanol | methanol | ethanol | ethanol | ethanol |
| Immersion temperature in impregnate containing metal compound (°C.) | 20 | 20 | 20 | 20 | 20 | 20 |
| Drying temperature after deposition of metal compound by adsorption (°C.) | 20 | 20 | 20 | 20 | 20 | 20 |
| Amount of silver deposited (% by weight) | 13.5 | 13.5 | 13.5 | 13.5 | 13.6 | 14.7 |
| Surface area of silver ($m^2/g$ of catalyst) | 1.03 | 1.03 | 1.03 | 1.03 | 1.25 | 2.42 |
| Exposed surface area of catalyst ($m^2/g$ of catalyst) | 0.14 | 0.14 | 0.14 | 0.14 | 0.36 | 1.18 |
| Adsorbed ion | cesium | rubidium | potassium | thallium | cesium | cesium |
| Amount (gram equivalent) of adsorbed ion per $m^2$ of surface area of silver | $2.3 \times 10^{-6}$ | $2.6 \times 10^{-6}$ | $2.8 \times 10^{-6}$ | $2.7 \times 10^{-6}$ | $2.9 \times 10^{-6}$ | $2.1 \times 10^{-6}$ |
| Reaction temperature (°C.) | 230 | 227 | 224 | 226 | 232 | 224 |
| Conversion (%) | 10.0 | 10.0 | 10.0 | 10.0 | 10.0 | 10.0 |

TABLE 1-continued

| | | | | | | |
|---|---|---|---|---|---|---|
| Selectivity (%) | 83.1 | 82.3 | 81.2 | 82.4 | 82.9 | 82.3 |

| | Example | | | Control | | |
|---|---|---|---|---|---|---|
| | 7 | 8 | 9 | 1 | 2 | 3 |
| Specific surface area of carrier ($m^2/g$) | 3.53 | 0.78 | 0.78 | 0.78 | 0.78 | 0.78 |
| Apparent porosity of carrier (%) | 62 | 57 | 57 | 57 | 57 | 57 |
| Impregnant (Solute) containing metal compound | cesium carbonate | cesium carbonate | cesium carbonate | cesium carbonate | cesium carbonate | cesium carbonate |
| (Solvent) | ethanol | ethanol | ethanol | ethanol | ethanol | ethanol |
| Immersion temperature in impregnate containing metal compound (°C.) | 20 | 0 | 20 | 20 | 20 | 70 |
| Drying temperature after deposition of metal compound by adsorption (°C.) | 20 | 0 | 20 | 20 | 20 | 70 |
| Amount of silver deposited (% by weight) | 14.8 | 13.5 | 13.5 | 13.5 | 13.5 | 13.5 |
| Surface area of silver ($m^2/g$ of catalyst) | 2.86 | 1.03 | 0.91 | 1.03 | 1.03 | 1.03 |
| Exposed surface area of catalyst ($m^2/g$ of catalyst) | 1.58 | 0.14 | 0.22 | 0.14 | 0.14 | 0.14 |
| Adsorbed ion | cesium | cesium | cesium | cesium | cesium | cesium |
| Amount (gram equivalent) of adsorbed ion per $m^2$ of surface area of silver | $2.0 \times 10^{-6}$ | $2.4 \times 10^{-6}$ | $2.3 \times 10^{-6}$ | $5.5 \times 10^{-6}$ | $0.4 \times 10^{-6}$ | $0.8 \times 10^{-6}$ |
| Reaction temperature (°C.) | 223 | 231 | 232 | 260 | 211 | 216 |
| Conversion (%) | 10.0 | 10.0 | 10.0 | 5.0 | 10.0 | 10.0 |
| Selectivity (%) | 82.2 | 83.2 | 82.9 | 73.5 | 72.0 | 76.0 |

EXAMPLE 10

A silver impregnant was prepared by mixing 420 g of silver oxalate with 200 g of water to produce a slurry, keeping the slurry cooled in a water bath, adding 360 g of ethanolamine to the cooled slurry, and thoroughly stirring the resulting mixture. In the impregnant was immersed 2.2 liters of α-alumina carrier having an apparent porosity of 55% and a BET specific surface area of 0.70 $m^2/g$. The impregnation mixture was stirred and heated to 90° C. for 1 hour, then heated further to 120° C., and stirred for 1 hour so as to have the reduced silver dispersed and deposited on the carrier. The silver-deposited catalyst was heated in a current of air at 260° C. for 24 hours.

Then, this catalyst was kept immersed in a solution of 1.16 g of cesium carbonate in 1,580 ml of reagent grade ethanol at 20° C. for 3 hours. Subsequently, the catalyst was deprived of excess impregnant and further swept with dry nitrogen flowing at a rate of 50 liters/minute for 5 hours for thorough evaporation and expulsion of the solvent remaining within the pores of the carrier. In this while, the temperature of the catalyst was prevented from exceeding 20° C.

The catalyst consequently obtained was found to have 13.2% by weight of silver deposited thereon. The surface area of this silver was 0.50 $m^2/g$ of catalyst, the exposed surface area of the carrier was 0.36 $m^2/g$ of catalyst, and the amount of cesium ion deposited by adsorption on the silver was $2.0 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

EXAMPLE 11

A catalyst was prepared following the procedure of Example 10, except that a solution of 0.95 g of rubidium carbonate in 1,580 ml of reagent grade methanol was used in place of the solution of 1.16 g of cesium carbonate in 1580 ml of reagent grade ethanol. The catalyst thus obtained was found to have 13.2% by weight of silver deposited thereon. The surface area of the silver was 0.50 $m^2/g$ of catalyst, the exposed surface area of the carrier was 0.36 $m^2/g$ of catalyst, and the amount of rubidium ion deposited by adsorption on the silver was $2.3 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

EXAMPLE 12

A catalyst was prepared following the procedure of Example 10, except that a solution of 0.95 g of potassium nitrate in 1580 ml of reagent grade methanol was used in place of the solution 1.16 g of cesium carbonate in 1580 ml of regent grade ethanol. The catalyst thus obtained was found to have 13.2% by weight of silver deposited thereon. The surface area of the silver was 0.50 $m^2/g$ of catalyst, the exposed surface area of the carrier was 0.36 $m^2/g$ of catalyst, and the amount of potassium ion deposited by adsorption on the silver was $2.4 \times 10^{-6}$ gram equivalent per the unit area, $m^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

EXAMPLE 13

A catalyst was prepared following the procedure of Example 10, except that 2.00 g of thallium acetate was used in place of 1.16 g of cesium carbonate. The catalyst thus obtained was found to have 13.2% by weight of silver deposited thereon. The surface area of the silver was 0.50 m$^2$/g of catalyst, the exposed surface area of the carrier was 0.36 m$^2$/g of catalyst, and the amount of thallium (monovalent) ion deposited by adsorption on the silver was 2.5×10$^{-6}$ gram equivalent per the unit area, m$^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

EXAMPLE 14

A catalyst was prepared following the procedure of Example 10, except that an α-alumina carrier having an apparent porosity of 53% and a BET specific surface area of 1.05 m$^2$/g was used instead and a solution of 2.0 g of cesium carbonate in 1,560 ml of reagent grade ethanol was used in place of the solution of 1.16 g of cesium carbonate in 1,580 ml of reagent grade ethanol.

The catalyst thus obtained was found to have 13.63 % by weight of silver deposited thereon. The surface area of the silver was 0.60 m$^2$/g of catalyst, the exposed surface area of the carrier was 0.60 m$^2$/g of catalyst, and the amount of cesium ion deposited by adsorption on the silver was 2.6×10$^{-6}$ gram equivalent per the unit area, m$^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

EXAMPLE 15

A catalyst was prepared following the procedure of Example 10, except that the impregnation temperature of the ethanol solution of cesium carbonate and upper limit temperature of the catalyst bed during drying was changed from 20° C. to 0° C. and flowing time of nitrogen during drying was changed from 5 hours to 8 hours.

The catalyst thus obtained was found to have 13.2% by weight of silver deposited thereon. The surface area of the silver was 0.50 m$^2$/g of catalyst, the exposed surface area of the carrier was 0.36 m$^2$/g of catalyst, and the amount of cesium ion deposited by adsorption on the silver was 2.1×10$^{-6}$ gram equivalent per the unit area, m$^2$, of the surface of the silver.

When oxidation of ethylene was carried out by using this catalyst following the procedure of Example 1, the results of 30 days' reaction were as shown in Table 2. Even after 6 months' continued reaction, this catalyst retained the performance thereof intact.

CONTROL 4

A silver-deposited catalyst obtained following the procedure of Example 10 was kept immersed in a solution of 4.50 g of cesium carbonate in 1,580 ml of reagent grade ethanol at 20° C. for 3 hours. Subsequently, the catalyst was deprived of excess impregnant and further swept with dry nitrogen flowing at a rate of 50 liters/minute for 5 hours for thorough evaporation and expulsion of the solvent remaining within the pores of the carrier. In this while, the temperature of the catalyst was prevented from exceeding 20° C.

The catalyst consequently obtained was found to have 13.2% by weight of silver deposited thereon. The surface area of the silver was 0.50 m$^2$ exposed surface area of the carrier was 0.36 m$^2$/g of catalyst, and the amount of cesium ion deposited by adsorption on the silver was 6.1×10$^{-6}$ gram equivalent per the unit area, m$^2$, of the surface of the silver.

When oxidation of ethylene was carried out by using this catalyst following the procedure of Example 1, the results of 30 days' reaction were as shown in Table 2.

CONTROL 5

A silver-deposited catalyst prepared following the procedure of Example 10 was kept immersed in a solution of 0.22 g of cesium carbonate in 1,580 ml of reagent grade ethanol at 20° C. for 3 hours. Then, the catalyst was deprived of excess impregnant and further swept with dry nitrogen flowing at a rate of 50 liters/minute for 5 hours for thorough evaporation and expulsion of the solvent remaining within the pores of the carrier. In this while, the temperature of the catalyst was prevented from exceeding 20° C.

The catalyst consequently obtained was found to have 13.2% by weight of silver deposited thereon. The surface area of the silver was 0.50 m$^2$/g of catalyst, the exposed surface area of the carrier was 0.36m$^2$/g of catalyst, and the amount of cesium ion deposited by adsorption on the silver was 0.4×10$^{-6}$ gram equivalent per the unit area, m$^2$, of the surface of the silver.

When oxidation of ethylene was carried out by using this catalyst following the procedure of Example 1, the results of 30 days' reaction were as shown in Table 2.

CONTROL 6

A silver catalyst prepared following the procedure of Example 10 was kept immersed in a solution of 1.16 g of cesium carbonate in 1,580 ml of reagent grade ethanol at 70° C. for 3 hours. Then, the catalyst was deprived of excess impregnant and further swept with dry nitrogen flowing at a rate of 50 liters/minute for 3 hours for thorough evaporation and expulsion of the solvent remaining within the pores of the carrier. In this while, the temperature of the catalyst was kept at 70° C.

The catalyst consequently obtained was found to have 13.2% by weight of silver deposited thereon. The surface area of the silver was 0.50 m$^2$/g of catalyst, the exposed surface area of the carrier was 0.36 m$^2$/g of catalyst, and the amount of cesium ion deposited by adsorption on the silver was 0.8×10$^{-6}$ gram equivalent per the unit area, m$^2$, of the surface of the silver.

When oxidation of ethylene was carried out by using the catalyst following the procedure of Example 1, the results of 30 days' reaction were as shown in Table 2. After six months' continued reaction using this catalyst, the reaction temperature increased 3° C. and the selectivity decreased to 73.0%.

TABLE 2

|  | Example | | | | | | Control | | |
| --- | --- | --- | --- | --- | --- | --- | --- | --- | --- |
|  | 10 | 11 | 12 | 13 | 14 | 15 | 4 | 5 | 6 |
| Specific surface area of carrier (m$^2$/g) | 0.70 | 0.70 | 0.70 | 0.70 | 1.05 | 0.70 | 0.70 | 0.70 | 0.70 |
| Apparent porosity of carrier (%) | 55 | 55 | 55 | 55 | 53 | 55 | 55 | 55 | 55 |

TABLE 2-continued

|  | Example | | | | | | Control | | |
| --- | --- | --- | --- | --- | --- | --- | --- | --- | --- |
|  | 10 | 11 | 12 | 13 | 14 | 15 | 4 | 5 | 6 |
| Impregnant (Solute) containing metal compound | cesium carbonate | rubidium carbonate | potassium nitrate | thallium acetate | cesium carbonate | cesium carbonate | cesium carbonate | cesium carbonate | cesium carbonate |
| (Solvent) | ethanol | methanol | methanol | ethanol | ethanol | ethanol | ethanol | ethanol | ethanol |
| Immersion temperature in impregnate containing metal compound (°C.) | 20 | 20 | 20 | 20 | 20 | 0 | 20 | 20 | 70 |
| Drying temperature after deposition of metal compound by adsorption (°C.) | 20 | 20 | 20 | 20 | 20 | 0 | 20 | 20 | 70 |
| Amount of silver deposited (% by weight) | 13.2 | 13.2 | 13.2 | 13.2 | 13.6 | 13.2 | 13.2 | 13.2 | 13.2 |
| Surface area of silver (m$^2$/g of catalyst) | 0.50 | 0.50 | 0.50 | 0.50 | 0.60 | 0.50 | 0.50 | 0.50 | 0.50 |
| Exposed surface area of catalyst (m$^2$/g of catalyst) | 0.36 | 0.36 | 0.36 | 0.36 | 0.60 | 0.36 | 0.36 | 0.36 | 0.36 |
| Adsorbed ion | cesium | rubidium | potassium | thallium | cesium | cesium | cesium | cesium | cesium |
| Amount (gram equivalent) of adsorbed ion per m$^2$ of surface area of silver | $2.0 \times 10^{-6}$ | $2.3 \times 10^{-6}$ | $2.4 \times 10^{-6}$ | $2.5 \times 10^{-6}$ | $2.6 \times 10^{-6}$ | $2.1 \times 10^{-6}$ | $6.1 \times 10^{-6}$ | $0.4 \times 10^{-6}$ | $0.8 \times 10^{-6}$ |
| Reaction temperature (°C.) | 231 | 229 | 226 | 228 | 234 | 232 | 260 | 212 | 219 |
| Conversion (%) | 7.5 | 7.5 | 7.5 | 7.5 | 7.5 | 7.5 | 3.9 | 7.5 | 7.5 |
| Selectivity (%) | 83.1 | 82.2 | 80.9 | 82.2 | 82.8 | 83.3 | 70.8 | 72.5 | 76.8 |

As already described in detail above, the conventional method which obtains a catalyst by the addition of a reaction promoter pays absolutely no consideration to the dispersion and deposition of at least one metal ion selected from the group consisting of cesium, rubidium, potassium, and thallium (monovalent) on the surface of silver and, with respect to the range of amount considered effective, only specifies a superficial amount departing far from the substantial truth. Thus, the catalyst produced by the conventional method fails to acquire satisfactory performance or sufficient catalyst life. The catalyst of the present invention realizes heretofore unattainable high selectivity and long catalyst life and, therefore, enjoys great economic advantage.

What is claimed is:

1. A silver catalyst, having finely divided silver particles dispersed by rapid deposition upon the outer surface of a porous inorganic refractory carrier and upon the inner wall surface of the pores of said carrier for use in the production of ethylene oxide by the catalytic gas phase oxidation of ethylene with molecular oxygen, said catalyst being prepared by a method comprising the steps of:
   impregnating said porous inorganic refractory carrier with a solution of a silver compound containing a thermally activateable reducing compound,
   thermally reducing the said impregnated carrier whereby finely divided silver particles are rapidly deposited and dispersed upon the outer surface of said porous inorganic refractory carrier and on the inner wall surfaces of the pores thereof,
   washing the resultant composite carrier with at least one member selected from the group consisting of water and lower alcohols,
   drying the said washed composite at a temperature of between 50° and 150° C.,
   rapidly depositing and dispersing upon the said freshly deposited silver upon the surface of said composite between $1 \times 10^{-6}$ and $5 \times 10^{-6}$ gram equivalents of cesium ion per square meter of surface of said composite,
   wherein said deposition and dispersion is effected by absorption of the said cesium ion from an impregnant solution containing the same,
   removing the impregnant from said composite and expelling the remaining solvent therefrom in a drying step carried out at a temperature not exceeding 50° C.

2. A silver catalyst according to claim 1, wherein said silver is deposited in an amount in the range of 5 to 25% by weight based on said catalyst.

3. A silver catalyst according to claim 2, wherein said silver particles have an average diameter of not more than 2,000 Angstroms.

4. A silver catalyst according to claim 1, wherein said porous inorganic carrier has an apparent porosity in the range of 40 to 70% and a BET specific surface area in the range of 0.1 to 10m$^2$/g.

5. A silver catalyst according to claim 4, wherein said porous inorganic carrier is α-alumina.

6. A silver catalyst according to claim 2, wherein said metal compound is selected from the group consisting of nitrates, sulfates, carbonates, oxalates, hydroxides, oxides, and acetates.

7. A silver catalyst according to claim 2, wherein said metal ion is deposited in an amount in the range of $1.5 \times 10^{-6}$ to $4 \times 10^{-6}$ gram equivalent per the unit surface area, m$^2$, of said silver.

8. A silver catalyst according to claim 2, wherein said metal ion is cesium ion.

9. A method of preparing a silver catalyst having finely divided silver particles dispersed by rapid deposition upon the outer surface of a porous inorganic refractory carrier and upon the inner wall surface of the pores of said carrier for use in the production of ethylene oxide by the catalytic gas phase oxidation of ethylene with molecular oxygen, comprising the steps of:
   impregnating said porous inorganic refractory carrier with a solution of a silver compound containing a thermally activateable reducing compound,
   thermally reducing the said impregnated carrier whereby finely divided silver particles are rapidly deposited and dispersed upon the outer surface of said porous inorganic refractory carrier and on the inner wall surfaces of the pores thereof,
   washing the resultant composite carrier with at least one member selected from the group consisting of water and lower alcohols, drying the said washed composite at a temperature of between 50° and 150° C., rapidly depositing and dispersing upon the said freshly deposited silver upon the surface of said composite between $1 \times 10^{-6}$ and $5 \times 10^{-6}$ gram equivalents of cesium ion per square meter of surface of said composite, wherein said deposition and dispersion is effected by absorption of the said cesium ion from an impregnant solution containing the same, removing the impregnant from said composite and expelling the remaining solvent therefrom in a drying step carried out at a temperature not exceeding 50° C.

10. A method according to claim 9, wherein said impregnation and said expulsion of the solvent by drying subsequent to the step of adsorption and deposition are carried out at temperatures in the range of 0° to 40° C.

11. A method according to claim 9, wherein a solvent constituting said solution containing a metal ion compound is a lower alcohol having not more than 3 carbon atoms or a mixed solvent thereof.

12. A method according to claim 9, wherein said solution of silver containing a reducing compound is selected from the group consisting of solutions having said silver compound dissolved in alkanolamine or other amine and containing an alkanolamine as a reducing compound, an aqueous silver nitrate solution containing formalin as a reducing compound, and solutions having silver nitrate dissolved in monoethylene glycol containing a lower acid amide as a reducing compound.

13. A method according to claim 9, wherein said silver is deposited in an amount in the range of 5 to 25% by weight based on said catalyst.

14. A method according to claim 13, wherein said silver particles have an average diameter of not more than 2,000 Angstroms.

15. A method according to claim 9, wherein said porous inorganic carrier has an apparent porosity in the range of 40 to 70% and a BET specific surface area in the range of 0.1 to $10 M^2/g$.

16. A method according to claim 15, wherein said porous inorganic carrier is α-alumina.

17. A method according to claim 13, wherein said metal compound is selected from the group consisting of nitrates, sulfates, carbonates, oxalates, hydroxides, oxides, and acetates.

18. A method according to claim 13, wherein said metal ion is deposited in an amount in the range of $1.5 \times 10^{-6}$ to $4 \times 10^{-6}$ gram equivalent per the unit surface area, $m^2$, of said silver.

* * * * *